(12) United States Patent
Stuckensen et al.

(10) Patent No.: US 9,649,816 B2
(45) Date of Patent: May 16, 2017

(54) PRODUCTION OF MATERIALS HAVING AN ANISOTROPIC STRUCTURE

(71) Applicant: Julius-Maximilians-Universitaet Wuerzburg, Wuerzburg (DE)

(72) Inventors: Kai Stuckensen, Wuerzburg (DE); Uwe Gbureck, Mellrichstadt (DE); Juergen Groll, Wuerzburg (DE)

(73) Assignee: JULIUS-MAXIMILIANS-UNIVERSITAET WUERZBURG, Wuerzburg (DE)

( * ) Notice: Subject to any disclaimer, the term of this patent is extended or adjusted under 35 U.S.C. 154(b) by 0 days.

(21) Appl. No.: 14/363,753

(22) PCT Filed: Dec. 10, 2012

(86) PCT No.: PCT/EP2012/074980
§ 371 (c)(1),
(2) Date: Jun. 6, 2014

(87) PCT Pub. No.: WO2013/083844
PCT Pub. Date: Jun. 13, 2013

(65) Prior Publication Data
US 2014/0350331 A1    Nov. 27, 2014

(30) Foreign Application Priority Data

Dec. 8, 2011    (DE) .................. 10 2011 120 488

(51) Int. Cl.
*B29C 67/20*      (2006.01)
*A61L 27/56*      (2006.01)
(Continued)

(52) U.S. Cl.
CPC .......... *B29C 67/202* (2013.01); *A61F 2/0063* (2013.01); *A61F 2/0077* (2013.01);
(Continued)

(58) Field of Classification Search
CPC .................. B29C 67/202; C08J 9/26
(Continued)

(56) References Cited

U.S. PATENT DOCUMENTS 5,738,860 A * 4/1998 Schønfeldt ........ A61F 13/00063
424/402
6,355,699 B1 * 3/2002 Vyakarnam ............. A61L 15/26
424/443

(Continued)

FOREIGN PATENT DOCUMENTS

DE       272699 A1    10/1989
DE    19751031 A1     6/1999
(Continued)

OTHER PUBLICATIONS

Mulder et al., Anisotropic Porous Biodegradable Scaffolds for Musculoskeletal Tissue Engineering, Oct. 29, 2009, Materials 2009, pp. 1674-1696.*

(Continued)

*Primary Examiner* — Atul P. Khare
(74) *Attorney, Agent, or Firm* — Viksnins Harris & Padys PLLP

(57) ABSTRACT

The present invention relates to a process for the production of a multi-layered material having anisotropic pores. It further relates to a multi-layered material which can be produced by the process according to the invention, and to the use of a multi-layered material as a chondral support matrix, a meniscus support matrix or an intervertebral disc support matrix.

19 Claims, 9 Drawing Sheets

(51) Int. Cl.
*C08J 9/26* (2006.01)
*C08J 9/28* (2006.01)
*A61L 27/20* (2006.01)
*A61L 27/22* (2006.01)
*A61L 27/38* (2006.01)
*A61F 2/00* (2006.01)
*A61F 2/28* (2006.01)
*A61F 2/02* (2006.01)

(52) U.S. Cl.
CPC ............... *A61F 2/28* (2013.01); *A61L 27/20* (2013.01); *A61L 27/22* (2013.01); *A61L 27/3817* (2013.01); *A61L 27/56* (2013.01); *C08J 9/26* (2013.01); *C08J 9/28* (2013.01); *A61F 2002/0081* (2013.01); *A61L 2430/06* (2013.01); *C08J 2201/026* (2013.01); *C08J 2201/0422* (2013.01); *C08J 2201/05* (2013.01); *C08J 2205/04* (2013.01); *C08J 2305/00* (2013.01); *C08J 2389/00* (2013.01); *Y10T 428/249975* (2015.04); *Y10T 428/249981* (2015.04)

(58) Field of Classification Search
USPC .......................................... 264/28, 49, 327
See application file for complete search history.

(56) References Cited

U.S. PATENT DOCUMENTS

| | | | |
|---|---|---|---|
| 6,447,701 B1* | 9/2002 | Heschel | A61L 15/425 |
| | | | 264/28 |
| 9,155,818 B2* | 10/2015 | Tampieri | |
| 2003/0023318 A1* | 1/2003 | Simmoteit | A61L 27/56 |
| | | | 623/23.76 |
| 2003/0078532 A1* | 4/2003 | Ruszczak | A61L 15/225 |
| | | | 602/46 |
| 2003/0209486 A1 | 11/2003 | Kools | |
| 2009/0232875 A1* | 9/2009 | Tampieri | A61L 27/24 |
| | | | 424/444 |

FOREIGN PATENT DOCUMENTS

| | | |
|---|---|---|
| DE | 602004000347 T2 | 7/2006 |
| EP | 1858562 B1 | 11/2009 |
| WO | WO 2008/103017 A1 | 8/2008 |

OTHER PUBLICATIONS

Bauer, M. et al.—*Journal of Chemical Physics*, 131, 224514, 8 pages (2009).
Blackford, J.R.—*Journal of Physics*, 40, R355-R385 (2007).
Damink, L.H.H.O. et al.—*Biomaterials*, 17, 765-773 (1996).
Deville, S. et al.—*Science*, 311, 515-518 (2006).
Deville, S. et al.—*Biomaterials*, 27, 5480-5489 (2006).
Grafahrend, K.-H. et al.—*Nature Materials*, 10, 67-73 (2011).
Heyer, H.—*Anaewandte Chemie*, 78, 130-141 (1966) [English Translation Included].
Ishiguro, H. and Rubinsky B.—*Cryobiology*, 31, 483-500 (1994).
Klein, T.J. et al.—*Macromolecular Bioscience*, 9, 1049-1058 (2009).
Knott, et al.—*Bone*, vol. 22 (3), 181-187 (1998).
Munch, E. et al.—*Biological Material Science*, 54-58 (2008).
Munch, E. et al.—*Journal of the American Ceramic Society*, 92 (7), 1534-1539 (2009).
Peppin, S.S.L.—*Proceedings of the Royal Society A*, 463, 723-733 (2007).
Suwanprateeb, J.—*Polymer International*, 55, 57-62 (2006).
Tampieri, A. et al.—*Biomaterials*, 29, 3539-3546 (2008).
http://education.vetmed.vt.edu/Curriculum/VM8054/Labs/Lab7/CASES/OCD/OCDDISCUSS.htm, 3 pages (2010).
Weadock, K.S. et al.—*Biomedical Materials Research*, vol. 29, 1373-1379 (1995).

* cited by examiner

US 9,649,816 B2

PRODUCTION OF MATERIALS HAVING AN ANISOTROPIC STRUCTURE

RELATED APPLICATIONS

This application is a 371 National Stage Application of International Application Number PCT/EP2012/074980, filed 10 Dec. 2012, which claims priority to European Application Number 10 2011 120 488.5 that was filed on 8 Dec. 2011, the contents of which are incorporated by reference herein.

FIELD OF THE INVENTION

The invention relates to the field of production of materials, in particular the production of medical materials.

BACKGROUND OF THE INVENTION

Medical materials are used, for example, for implants, microsensors and other products which are placed in the human or animal body. In this context the medical materials directly come into contact with the tissue and the cells of the body. In their natural environment cells are surrounded by an extracellular matrix which is important for the survival of the cells, since it decisively influences their adhesion, proliferation, migration, differentiation and function. The main components of the extracellular matrix are hydrogels and polymer fibres which are not water-soluble, these serving as a mechanical scaffold. Basal membranes and ultrathin separating layers between tissues are also present. These structures are matched to the different biological requirements of various organs and tissues. In order to promote a good interaction between the cells and the medical materials, attempts are made to adapt the structure and composition of the materials to the natural environment of the cells.

DE 19751031 A1 describes highly pure collagen sponge products having an open pore structure which shall enable growth of the cells into the sponge. A freezing process with which a homogeneous and targeted distribution of the collagen fibres in channel-like guiding structures is generated by finger-shaped ice crystals growing through a collagen type I dispersion is used for production of the collagen sponges. For this, analogously to the common processes of metalworking, freezing processes have been designed which structure a mixture of substances between two temperature-controllable surfaces which are arranged parallel or concentrically with respect to one another by keeping the temperature gradient between the surfaces constant. The mixture structured in this manner is then freeze-dried by precooling it under overpressure and releasing the pressure suddenly. However, the materials obtained in this way exclusively consist of one single functional component, namely collagen type I, and therefore can reproduce the natural environment of cells to only a limited extent.

Tampieri et al., 2008 describe the combination of three layers of collagen scaffolds of different composition to form an overall structure, each scaffold representing a different bone or cartilage layer. The top layer consists of pure collagen I and serves as a chondral zone replacement. Collagen I mineralized by a precipitation reaction with hydroxylapatite, with a mineral-matrix ratio of 70/30 wt. %, replaces the subchondral bone. However, an intermediate layer mineralized in the same manner, in a mineral-matrix ratio of 40/60 wt. %, differs significantly from the tidemark of native chondral tissue. The hydroxylapatite of the subchondral zone here is partially doped by magnesium. The individual collagen scaffolds were each crosslinked separately by 1,4-butanediol diglycidyl ether (BDDGE) and bonded to one another using a "weaving process". The overall structure was then freeze-dried. Cell experiments showed, however, that the structure produced in this way allows only a limited population by cells. Thus, only a low cell migration into the inside of the chondral replacement zone with a non-uniform distribution was to be observed, whereas the region in the centre of the scaffold remained substantially acellular. A complete integration of the material after implantation is therefore not possible.

EP 1858562 B1 describes a porous, three-layered, osteochondral scaffold. This comprises a zone covered with a smooth surface, which is made to the extent of 100% of collagen I of equine origin and shall correspond to chondral tissue. The region of the subchondral and osteal zone is represented by composites of collagen type I and nanostructured, magnesium-enriched hydroxylapatites. The individually produced zones, however, are joined together only subsequently by a compression operation, as a result of which a delamination may occur during rehydration of the freeze-dried matrices. Moreover, histological results of animal studies show that only fibrous chondral tissue but no native articular chondral tissue is formed in the chondral zone. Such fibrous chondral tissue is formed above all during the natural but rare and incomplete self-healing processes of the cartilage. In addition to the collagen type II mainly occurring in healthy articular cartilage, it also comprises atypical collagen type I and differs decisively in structure and functionality from native chondral tissue. The adverse formation of fibrous chondral tissue is possibly to be attributed to the fact that the chondral replacement zone only consists of one individual layer, which has an atypical composition compared with native cartilage and too large porosities with an unnatural alignment.

There is therefore the need for stable materials which have functionally different regions which reproduce the natural environment of cells.

SUMMARY OF THE INVENTION

The invention relates to a process for the production of a multi-layered material having anisotropic pores, comprising the steps of providing a temperature gradient by two temperature-controllable bodies arranged opposite one another; arranging and solidifying in the temperature gradient a first substance which contains at least one sublimable compound in order to form a first layer; arranging and solidifying in the temperature gradient at least one further substance which contains at least one sublimable compound in order to form at least one further layer adjacent to the preceding layer; subliming the compound and consolidating the layers.

The invention also relates to a multi-layered material which can be produced by the process according to the invention, and to a medical material having at least two different layers, in which pores extend anisotropically through at least two layers of the material. The invention furthermore relates to the use of a multi-layered material as a chondral support matrix, a meniscus support matrix or an intervertebral disc support matrix in which pores extend anisotropically through at least two layers of the material.

DESCRIPTION OF THE FIGURES

FIG. 4 b shows a histological section, stained with haematoxylin-eosin, through the centre of the chondral zone of an alginate matrix populated for 21 days by human mesenchymal stem cells. After static cell population, the cells have migrated into the inside of the support matrix and have adhered there preferentially to microstructures within the pores. Synthesis products in the form of matrix formed by cells are already to be seen. FIG. 4 c shows a light microscopy image of a plan view of a collagen-based chondral support structure. The support matrix predominantly consists of collagen and chondroitin sulphate and is traversed by anisotropic, longitudinal pores. FIG. 4 d shows a scanning electron microscopy image of a cross-section through the support matrix of FIG. 4 c.

FIGS. 7 b and c show a monolithic, intervertebral disc-like support structure based on alginate, anisotropic lamellae characterizing the structure of the outer region of the support matrix.

DETAILED DESCRIPTION OF THE INVENTION

In a first aspect the invention relates to a process for the production of a multi-layered material having anisotropic pores, comprising the steps of providing a temperature gradient by two temperature-controllable bodies arranged opposite one another; arranging and solidifying in the temperature gradient a first substance which contains at least one sublimable compound in order to form a first layer; arranging and solidifying in the temperature gradient at least one further substance which contains at least one sublimable compound in order to form at least one further layer adjacent to the preceding layer; subliming the compound and consolidating the layers.

The process serves for production of a material which comprises several, that is to say at least two, preferably three, different layers which are combined to a monolith. The layers can differ in their composition, their functionality and their physical properties. Inasmuch they are similar to biological tissues, such as, for example, extracellular matrices, which likewise have regions or layers of different chemical composition and biological functionality. The materials produced by the process are accordingly suitable in particular for medical applications, also within the animal or human body. Due to the different layers they can reproduce the natural environment into which they are introduced, and where appropriate perform corresponding biological functions.

The different layers are formed by arranging several substances over one another or side by side and solidifying them. In order to obtain a continuous anisotropic pore structure, the substances are arranged on one another or side by side without the solidification process being interrupted.

Figure 1A:
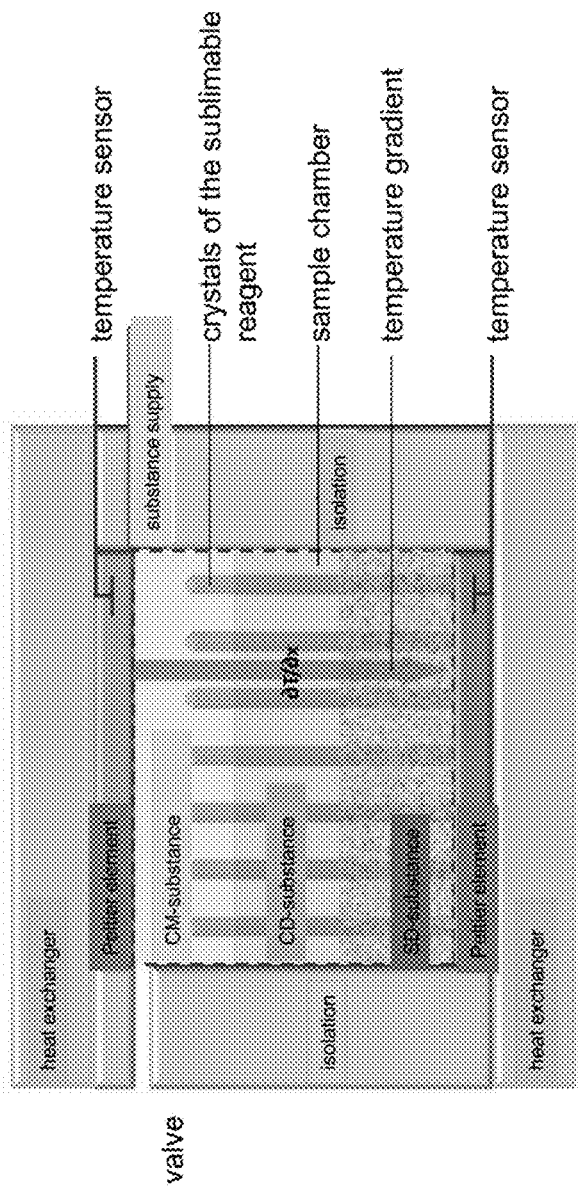
FIG. 1 shows the structure and the fundamental mode of functioning of a possible embodiment of a solidification apparatus. a) Simplified schematic representation of the mode of functioning. Peltier elements coupled to heat exchangers ensure, via a controlled external temperature gradient, an anisotropic crystal growth in the substances in the sample chamber. b) Assembling plan of a possible embodiment of a solidification apparatus. The sample chamber is in the centre of the insulation unit I1 and is in thermal contact with the temperature-controllable bodies W1 and W2, which are located above and below the sample chamber. The temperature-controllable bodies are within the insulation unit I2 and are coupled to the Peltier elements P1 and P2, which are fixed by the insulation units I3 and I4. This inner assembly is in the centre of the heat exchanger ring A2, which together with the heat exchanger units A1 and A3 forms an outer assembly.
Figure 1B:
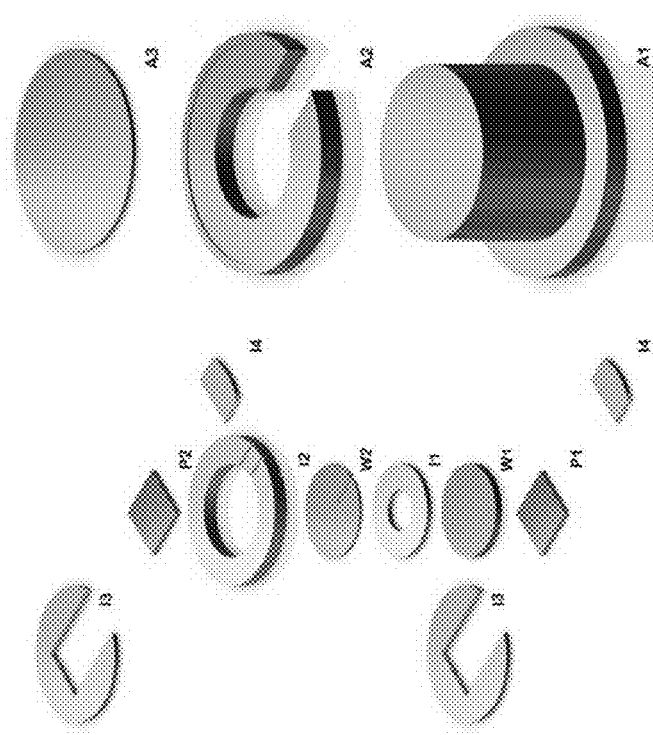

The substances are solidified by being arranged in a temperature gradient formed by two temperature-controllable bodies arranged opposite one another. A solidification process here is to be understood as meaning that the degrees of freedom for spatial movement of particles is restricted such that these can still move spatially to only a very small extent, if at all. In many cases this is accompanied by a phase conversion. The solidification can be carried out in an aligned or non-aligned manner, a macroscopically isotropic structure being formed in a non-aligned solidification and a macroscopically anisotropic structure being formed in an aligned solidification. By the substances being solidified in a directional temperature gradient, an aligned solidification occurs, the solidification starting at the points of the substances with the lowest temperature and moving with time in the direction of the points of the substances with the highest temperature. The solidification front thereby migrates uniformly through the substances. The process can be carried out, for example, with a solidification apparatus as shown in FIG. 1.

During solidifying, the sublimable compound in the substances forms crystals, which can likewise grow in an aligned manner along the temperature gradient. By the layers being arranged in succession, the crystals of the sublimable compound grow uniformly successively through all the layers (FIG. 1 a). Due to the sublimation, the crystals of the sublimable compound are removed from the layers formed, so that hollow pores remain. Because of the aligned solidification, the pores have an anisotropic structure and run continuously through all the layers. A continuous anisotropic pore structure enables the population of the material by cells as far as the inside, as a result of which a good integration and functionality of the material in the native tissue is enabled.

The solidified layers and polymer fibre layers applied can be consolidated by suitable processes by forming additional linkages between the polymers or between the structures formed by them. Due to these additional bonds a three-dimensional network is formed, which increases the hardness and stability of the material. The consolidating can be carried out by various chemical processes, for example by wet chemical crosslinking, dehydrothermal processes, enzymatic crosslinking, non-enzymatic glycation, UV irradiation, gamma irradiation, sintering, infiltration of the material or by a combination of various processes. The wet chemical crosslinking is preferably carried out by means of carbodiimides, isocyanates, complexing ions or glutaraldehyde, and further preferred under a pressure of ≤300 mbar. In a preferred embodiment consolidating the layers comprises a wet chemical crosslinking and a dehydrothermal process.

In a preferred embodiment the temperature gradient is between 0.5 K/mm and 200 K/mm, preferably between 2.5 K/mm and 25 K/mm, further preferred between 5 K/mm and 15 K/mm. Such gradients allow a continuous aligned crystal growth which leads to the formation of anisotropic pores. The temperature gradient is determined by the temperatures of the two temperature-controllable bodies and their distance from one another, one temperature-controllable body having the lowest temperature and the opposite one the highest temperature and thus generating the gradient. The temperature gradient decisively determines the rate at which the substances solidify and therefore also influences the formation of the crystals of the sublimable compound. Since the crystals of the sublimable compound directly determine the form and size of the pores, the shape of the pores can be influenced by the temperature gradient. Thus, for example, greater temperature gradients lead to the formation of smaller and narrower pores during solidifying of the same substance. Greater gradients therefore tend to be employed at lower temperatures. At lower temperatures, furthermore, greater temperature gradients may form if the warmer temperature level has an upper limit because of the possibility of protein denaturings. A small temperature gradient may lead to a slow rate of freezing, which promotes the formation of crystals having a columnar morphology. A rapid rate of freezing, on the other hand, may lead to the formation of dendritic crystals with many branchings. This can be utilized to reproduce a natural tissue structure which comprises both isotropically and anisotropically structured regions, such as, for example, an intervertebral disc. An isotropic pore structure can be generated by equiaxial dendritic crystal growth, while an anisotropic pore structure can be generated by columnar or dendritic crystal growth. Materials having anisotropic pores have a higher stability under the particular loads such as occur in specialized tissues compared with those having a non-aligned, isotropic pore structure, and have a higher compressive and tensile strength at the same porosity. Furthermore, anisotropic pores, in contrast to isotropic pores, allow an effective cell migration into the inside of the material. If the material is nevertheless to have isotropic pores, for example in order to reproduce a natural isotropic structure, this can be achieved by a non-aligned solidification of the substances. For this, the substances are solidified at a uniform temperature or with a very small temperature gradient of <0.5 K/mm. It is also possible to form regions or layers having an isotropic structure and those having an anisotropic structure within the same material by subjecting individual regions of the material to aligned or non-aligned solidification.

In a preferred embodiment the substances are solidified with a linearly interpolated cooling rate of from 2 K/min to 45 K/min, more preferred 5 K/min to 35 K/min. The cooling rate is to be understood as meaning the linear interpolation of the temperature difference per unit time of the substances to be solidified, from the start of the crystal growth to complete solidification.

In an advantageous embodiment the temperature gradient is constant during the process. This means that the temperature difference between the lowest temperature, that is to say the one temperature-controllable body, and the highest temperature, that is to say the temperature-controllable body arranged opposite, and the spatial distance between the two remain unchanged. A stable crystal growth through all the layers is thereby ensured. A constant temperature gradient also includes the lowest and the highest temperature, at a constant distance between the two temperature-controllable bodies, being increased or lowered in parallel.

In an advantageous embodiment of the process the temperature gradient, at a constant distance between the temperature-controllable bodies, is increased or reduced during the process by increasing or lowering the temperature of the temperature-controllable bodies. Preferably, this is carried out after the solidification of one or more layers and before feeding in a further substance.

In a preferred embodiment the lowest temperature of the temperature gradient is between −200° C. and +90° C. and the highest temperature of the temperature gradient is between +100° C. and −25° C. In a further preferred embodiment the lowest temperature of the temperature gradient is between −60° C. and −15° C. and the highest temperature of the temperature gradient is between +30° C. and +5° C. The lowest and the highest temperature of the gradient depend on the composition of the substances and the melting point of the sublimable compound. Compositions of high density, for example compositions having a high content of polymers, in particular solidify slowly and are therefore solidified under temperature gradients which are generated at lower temperatures. If the substances comprise a sublimable compound of low melting point, for example an organic solvent, the substances are preferably solidified at correspondingly low temperatures. If, on the other hand, sublimable compounds such as, for example, water or acetic acid, are used, higher temperatures are possible. Due to the constitutive supercooling at the solidification boundary, crystal formation of water at above 0° C. is also possible.

In a preferred embodiment the lowest and the highest temperature of the temperature gradient are constant during the process. The temperature gradient, that is to say the temperature of the two temperature-controllable bodies and their distance from one another, is set before arranging the first substance. During the solidification of the substances both the lowest and the highest temperature of the temperature gradient, that is to say the temperatures of the temperature-controllable bodies, and the distance of the bodies from one another remain unchanged. A lowering of the temperatures of the two temperature-controllable bodies at a constant temperature difference during the freezing operation is possible but not necessary.

The term "temperature-controllable bodies" describes both bodies which can actively remove heat, such as, for example, Peltier elements, and those bodies which indirectly remove heat by being cooled or supply heat by being heated. The temperature-controllable bodies are preferably made of metal or metal compounds. The bodies can be arranged both horizontally and vertically, in a horizontal arrangement the lower temperature-controllable body as a rule determining the lowest temperature of the temperature gradient. The temperature-controllable bodies can be present in individual geometries, for example as a negative form for the material to be produced. In addition to conventional forms, such as cuboids, cylinders, pyramids, cones, rotational ellipsoids, spheres, rings or subsets thereof in solid form or hollow body form, individualized forms are also possible. The latter can be produced, for example, according to information from three-dimensional imaging methods, such as x-ray tomography or magnetic resonance tomography, so that materials adapted individually for each patient can be produced. In addition to temperature-controllable bodies, insulating bodies can also be used for shaping the material. These are suitable above all for giving individual layers or the entire material an individual form. The temperature-controllable or insulating bodies can be in direct thermal contact with the substances.

In a preferred embodiment the substances are arranged in a container which is placed in the temperature gradient. In this case the material is formed within the container and its form is determined by the geometry thereof. Like the temperature-controllable and insulating bodies, the container can also serves as a negative form for the material and accordingly have the abovementioned forms.

In a preferred embodiment the first and/or further substance, independently of each other, is a solution, a dispersion, a suspension, a gel, a polymer melt, or a mixture thereof. The term "substance" describes the flowable precursors of the layers of the later material.

In a preferred embodiment the first and/or a further substance, independently of each other, contains at least one polymer or monomers thereof. The composition of the precursors determines the composition of the individual layers of the material. The constituents of the substances are therefore chosen according to the function and the properties which the individual layers are to have in the later material. Preferably, the layers correspond to the tissue which the material replaces or into which it is integrated. Polymers are preferred constituents of the substances, since they form stable structures and networks by intermolecular bonds.

Preferably, the polymer is a native polymer. In contrast to denatured polymers, native polymers are present in their natural secondary structure, which enables the molecule to the effective formation of complexes and networks, and can be recognized by cells as native environment. Furthermore, prepolymers and macromonomers can be used, the prepolymer being a synthetic (co)polymer having a molecular weight of less than 50 kDa, which in addition contains crosslinkable groups, such as, for example, (meth)acrylates, thiols, isocyanates, azides, ethynes, aldehydes, carboxylic acids and/or amines.

In a preferred embodiment the polymer is selected from the group consisting of peptides, proteins, preferably structural proteins, and polysaccharides. The polymer can be a polymer produced by synthesis. The use of proteinogenic polymers, in particular the use of structural proteins, is preferred above all for medical application, since these polymers are also present in the natural tissue matrix. By using such polymers for the production of the material it is possible to reproduce the body's own structures, also with respect to their chemical composition. Furthermore, proteinogenic polymers, in particular structural proteins, form stable networks, which are particularly suitable for the production of materials. Collagens form triple helices, which combine to form long fibres, while keratins form superhelices, which in turn form intermediate filaments. In addition to proteinogenic polymers, polysaccharides are also suitable for the formation of stable materials, since they likewise form intermolecular networks, such as microfibrils. The formation of such structures contributes decisively to the stability of the material. In addition to structure-forming polymers, the substances can also contain further constituents, for example of the extracellular matrix. The use of glycoaminoglycans, such as, for example, hyaluronic acid and chondroitin sulphate, which due to their high degree of hydration can store large amounts of water which exceed several times their own volume, is particularly preferred. Since the natural tissue matrix is highly water-retentive, it is advantageous to incorporate such compounds into the material. By using such polymers, furthermore, an electrostatic repulsion which occurs increasingly during deformation in an aqueous medium can be utilized, which can generate a shock-absorbing effect of the support matrix. The physical properties of the material are thereby adjusted to the natural tissue matrix.

In a preferred embodiment the polymer is selected from the group consisting of collagen type I, II, III, V, VI, IX, X, XI, XII, XIV, XVI, chondroitin sulphate, aggrecan, keratan sulphate, hyaluronic acid, proteoglycan 4, cartilage oligomeric matrix protein (COMP), fibromodulin, procollagen II, decorin, anchorin, hyaluronate, biglycan, thrombospondin, fibronectin, chondrocalcin, alginate, cellulose and chitosan, polylactic acid (D and/or L), polyglycollic acid, copolymers thereof, polycaprolactone, polyanhydrides, polyacetals and polyketals, polyethylene glycol, poly(meth)acrylates, poly (glycidol), aromatic polyesters, PET, polyoxacyclines, polyurethanes, polyvinyls, polyvinyl alcohols, cartilage fragments, collagen fibrils and mixtures thereof. The composition of the substances can be chosen according to the biochemical composition of the tissue which the material is to reproduce, for example different cartilage tissue or bone. For the production of model matrices, the polymer is preferably alginate.

In a preferred embodiment the substance contains 0.5 to 60 wt. % of polymer. As a result of the formation of the material being carried out by solidification and consolidation, different concentrations of polymers can be used. The polymer concentrations can correspond to the natural tissue which the material reproduces. For a high strength of the material, higher concentrations of polymers, above all of structural proteins, such as collagens, are preferred. In a further preferred embodiment the substance therefore contains 0.8 to 10 wt. % of polymer, preferably approx. 3 wt. % of polymer.

In a preferred embodiment the first and/or a further substance contains at least one compound selected from the group consisting of ceramics, salts, metal oxides, semi-metal oxides, non-metal oxides, catalysts, proteins, growth factors, medicinal active compounds, lipids, surfactants, buffer substances and mixtures thereof. According to the functions and physical properties which the layers of the finished material are to be given, one or more substances can contain further compounds. Compounds having a medicinal and/or biological action can preferably be integrated into medical materials. These include, for example, antibiotics, anti-inflammatories, antimycotics, β-lactams, such as penicillins, cephalosporins, monobactams and carbapenems, glycopeptides, such as vancomycins and teicoplanins, polyketides, such a tetracyclines and macrolides, polypeptides, such as polymyxins, bacitracin and tyrothricin, quinolones, sulphonamides, aminoglycosides, streptomycins, amphenicols, aureomycins, non-steroid anti-inflammatories, glucocorticoids and polyene antimycotics, such as amphotericin B. After implantation or placing of the material in the body, these compounds have a local action, which means that a systemic treatment, such as, for example, by enzyme inhibitors or immunorepressants, can be prevented or reduced. If the material is used for implantation purposes, for example as a support matrix for chondral defects, growth factors, such as TGF, BMP, GDF, FGF, IGF, annexin, MMP, PDGF, EGF, GMCSF, VEGF, HGF, interleukins, NGF and CSF, and/or compounds which promote the cell migration, are preferably integrated into the material. The migration of tissue cells into the material and the formation of extracellular matrix are thereby promoted. This can lead to integration of the material into the tissue and also to a complete re-establishment of the cartilage.

In a preferred embodiment the sublimable compound has a melting point of ≤450° C., preferably ≤90° C., further preferred from −200° C. to +30° C., further preferred from −100° C. to +20° C. Preferably, the sublimable compound is liquid at room temperature, which allows a simple processing and preparation of the substances.

In a preferred embodiment the sublimable compound is selected from the group consisting of aqueous solvents, polar solvents, non-polar solvents, organic acids, organic bases, mineral acids and mineral bases. The sublimable compound can be added to the already dissolved constituents of the substance or, if the other constituents of the substance are present as a solid, these can be dissolved in the sublimable compound. In this case the sublimable compound is preferably a solvent in which the other constituents of the substance, for example polymers, are dissolved. Structural proteins in particular are only sparingly soluble, so that they are preferably dissolved in a weak acid, for example in 0.25 to 5 M acetic acid, which also serves as the sublimable compound. The sublimable compound also influences the structure of the pores in the finished material, because these are formed by the crystals of the sublimable compound. Since the crystal structures of different sublimable compounds differ, the form of the pores, in particular their size and branching, can be influenced by the choice of the sublimable compound. In a preferred embodiment the sublimable compound is water. Water is particularly suitable as the sublimable compound since it is universally available and already crystallizes at comparatively high temperatures. Only a little cooling of the temperature-controllable bodies is therefore necessary in order to solidify the substances which contain water as the sublimable compound. As a result the entire process is advantageous in terms of energy and cost-effective.

In a further preferred embodiment the polar solvent is selected from the group consisting of ethanol, isopropanol, acetone, ether, dimethylsulphoxide, dimethylformamide, tetrahydrofuran, N-methyl-2-pyrrolidone, chloroform, 1,4-dioxane, acrylonitrile and acetonitrile.

In a further preferred embodiment the non-polar solvent is selected from the group consisting of benzene, toluene, methylene chloride, hexane, heptane and xylene.

In a further preferred embodiment the organic acid is selected from the group consisting of carboxylic acids, alkylcarboxylic acids, acetic acid, benzoic acid and alkylsulphonic acids.

In a further preferred embodiment the mineral acid is selected from the group consisting of sodium hydroxide solution, potassium hydroxide, lime water, phosphoric acid and hydrochloric acid.

In a preferred embodiment the first substance and at least one further substance, preferably every further substance, have the same sublimable compound. If two substances of adjacent layers contain the same sublimable compound, the crystals on the surface of the first, already solidified layer combine with the still liquid molecules of the sublimable compound in the second substance when this is applied to the already solidified layer. This promotes growing of the crystals which protrude beyond the first already rigid layer into the next layer. Moreover, the crystal structures in the layers become similar to one another if the same sublimable compound is used, as a result of which all the layers have uniform pores after the sublimation.

In a preferred embodiment at least one of the temperature-controllable or insulating bodies or the container has a microstructuring. The term "microstructuring" describes a structuring on the surface of a temperature-controllable or insulating body or of a container in the form of projections and/or depressions at a distance of a few micrometers. This structuring initiates the formation of crystallization nuclei, by means of which the points at which the crystallization or solidification first starts can be controlled. The solidification spreads out further from the crystallization nuclei, by means of which the spatial orientation of the crystals and therefore of the later pores can be controlled. By microstructurings in the form of concentric circles, curves, waves or lines, a corresponding arrangement of the pores within the material can be achieved. However, the microstructuring can also serve to configure the surface of the material, for example in order to promote the adhesion of cells on the material. If the microstructuring serves to control the crystallization, it is preferably applied to the temperature-controllable body or to the container in which the substances are introduced, each of which is arranged at the coldest point of the temperature gradient.

In a preferred embodiment the sublimation is carried out under a pressure of ≤6 mbar and at a temperature of ≤0° C., preferably under a pressure of from 10 Oar to 1 mbar and at a temperature of from −80° C. to −20° C., further preferred under a pressure of from 50 Oar to 90 μbar and at a temperature of from −60° C. to −30° C. Due to the sublimation, the sublimable compound which has crystallized out in the solidified layers is converted from its solid phase into the gas phase. The gas formed is sucked off, so that instead of the crystals of the sublimable compound hollow bodies in the form of pores remain. The sublimation pressure and the sublimation temperature depend on the sublimable compound used and can be obtained from temperature-phase diagrams. The sublimation of water is carried out under below 6 mbar and at below 0° C. These sublimation parameters are also suitable for aqueous solutions of acids or bases, for example for 0.25 to 5 M acetic acid.

In a preferred embodiment the process further comprises the step of arranging a layer of functionalized polymer fibres on the support matrix as outermost layer. The layer of functionalized polymer fibres can function as a friction-reducing surface, or final membrane. The function as a friction-reducing surface can be intensified by the use of lubricins. By a fibre alignment parallel to the material surface, shearing forces arising there can be processed better by the material. It can be generated by functionalized polymer fibres (e.g. collagen type I, II, III, V, VI, IX, X, XI, XII, XIV, XVI, or linear, branched or star-shaped polymers based on polyethylene glycol). The layer of functionalized polymer fibres can be applied to the material by means of electrostatic spinning, before or after consolidation thereof (Grafahrend et al., 2010).

Figure 2:
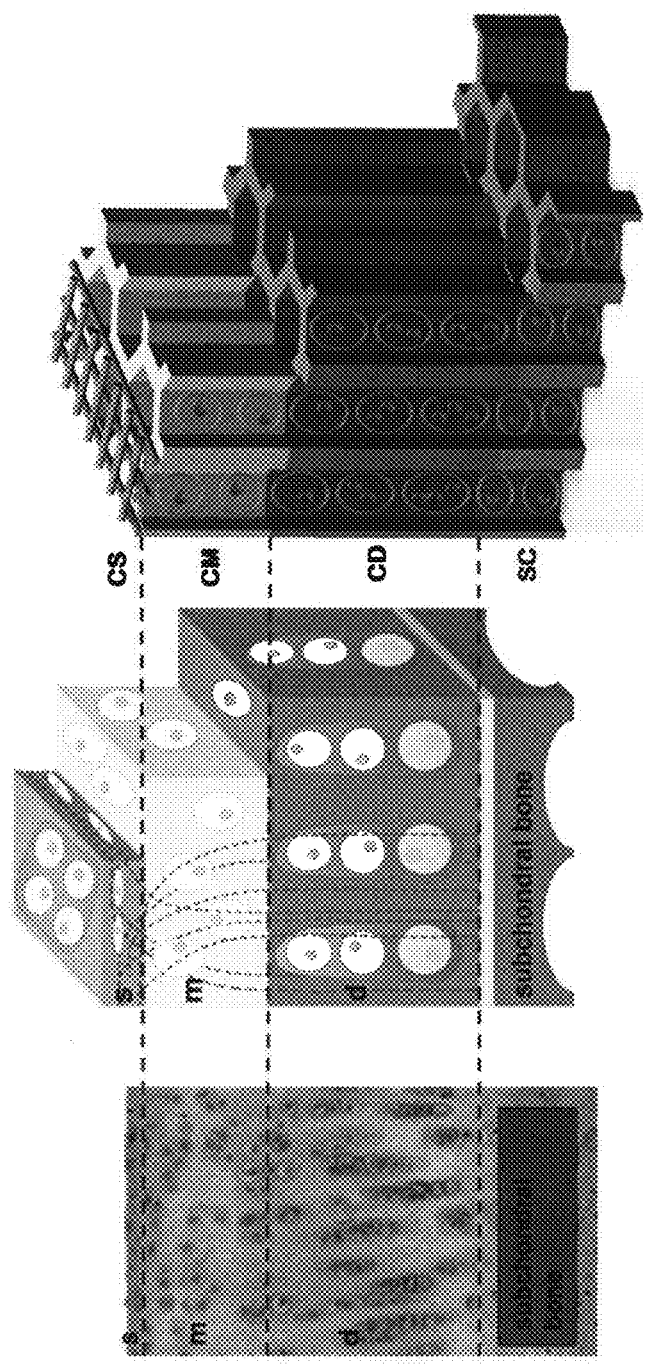
FIG. 2 shows a histological (left) and a schematic (middle) representation of the native articular cartilage structure with three distinguishable zones (s: superficial; m: middle; d: deep) (Klein et al., 2009), and a biomimetic support matrix built up in layers and having continuous pores (right). Broken lines running vertically in curves in the schematic representation of the articular cartilage structure symbolize the orientation of collagen fibres. The chondrocytes are adapted differently in their shape (spheroids) and organization to the specific requirements of the particular zone (s, m and d). In the support matrix the bone substitute composite (SC) is joined to a deeper chondral zone (CD), which passes into a middle chondral zone (CM). This is in turn joined to functionalized polymer fibres, which form a final sliding layer (CS).

In a further aspect the invention relates to a multi-layered material which can be produced by the process according to the invention. The material produced by the process comprises several layers which differ in their functionality, their composition and/or their physical properties. The various layers are combined to a monolith, that is to say one piece or a one-piece form, so that a monolithic structure having anisotropic pores is formed. In this manner the material combines several different regions and can thus meet complex requirements such as arise above all in the medical field. For example, the layered structure of a natural bone-cartilage structure can be reproduced with the material (FIG. 2). The material is moreover distinguished by an anisotropic pore structure which penetrates all the layers and imparts to it specific physical and biological properties. Due to the anisotropic pore structure the stability of the material is improved, and by the pores protruding through all the layers continuously, that is to say crossing the boundaries of the layers, the cohesion of the individual layers is promoted and a delamination is prevented. The pores furthermore enable the penetration of substances as far as into the inside of the material. A population of the material with cells is also possible due to the pores, since the continuous pores enable a migration of the cells as far as into the inside of the material. This is of importance above all for the use of the material as a bone/cartilage replacement for articular defects, since the population of the material with chondrocytes after implantation contributes towards the reconstruction of the cartilage and towards the complete integration of the implant. The material is moreover also particularly suitable for cultivation of cells, since it provides a three-dimensional structure which, in contrast to conventional two-dimensional cultivation vessels, imitates the natural environment of the cells. An adequate exchange of nutrients and toxins can likewise be effected due to the anisotropic pore structure.

In a preferred embodiment the pores have a columnar, lamellar and/or dendritic structure. The structure of the pores is determined by the nature of the sublimable compound, of the other constituents of the substances, and by the temperatures of the temperature-controllable bodies or the temperature gradient. A lamellar morphology here is to be understood as meaning a solidified phase of the sublimable additives which is arranged in the form of lamellae. A columnar morphology corresponds to a rod- or prism-shaped manifestation of the solidified phase of the sublimable additives. If ramifications or branches protrude out of side faces of a columnar morphology, this is a dendritically solidified phase of the sublimable additives. In contrast to columnar, lamellar and dendritic crystals, equiaxial crystals have a spherical dendritic structure. Columnar pore structures increase the stability of the material, so that this is more resistant to deformations. Lamellar pores, on the other hand, facilitate the population of the material with cells.

In a preferred embodiment the at least two layers have a different composition. Materials which have layers or regions with different compositions can perform several functionalities. This is of importance in particular for medical materials which are integrated into natural tissue. Most of the tissues in the human or animal body combine different properties or perform different functions by having various regions of different cellular or extracellular composition. This applies, for example, to the extracellular matrix, which on the one hand supports and holds together the organs, but also controls cell adhesion and stores water. By a medical material combining several layers of different chemical compositions, it can reproduce the multifunctionality of natural tissue, for example the natural extracellular matrix.

In a preferred embodiment the at least two layers independently of each other have at least one polymer. Polymers are preferred constituents of the layers since they form stable structures and networks by intermolecular bonds. Preferably, the polymer is a native polymer.

In a preferred embodiment the pores have a diameter of from 20 µm to 380 µm, preferably from 50 µm to 120 µm, further preferred of approx. 80 µm. In order to ensure an efficient population of the material by cells, the pores should have a diameter of at least 20 µm. For materials in particular which are used as a (bone)-cartilage replacement, pores having a larger diameter, for example of from 60 µm to 100 µm, are advantageous because they not only enable the migration of the cells into the inside of the material, they also leave space for the formation of extracellular matrix inside the material. Interestingly, an efficient population of materials having relatively narrow pore chambers, for example having diameters of from 20 µm to 50 µm, is also possible if the composition of the materials is particularly similar to the natural extracellular matrix.

In a further aspect the invention relates to a medical material having at least two different layers, in which pores extend anisotropically through at least two layers of the material. The medical material can be produced by the process according to the invention and can be present in the preferred embodiments described above for a multi-layered material.

In a further aspect the invention relates to the use of a multi-layered material as a medical material in which pores extend anisotropically through at least two layers of the material. The material can be produced by the process according to the invention and can be present in the preferred embodiments described above for a multi-layered material.

In a further aspect the invention relates to the use of a multi-layered material as a medical support matrix in which pores extend anisotropically through at least two layers of the material. Due to the anisotropic pore structure which extends beyond the boundaries of the layers through the entire material, this is particularly suitable as a medical support matrix because a complete population of the material by cells is possible.

In a further aspect the invention relates to the use of a multi-layered material as a(n) (osteo)chondral support matrix in which pores extend anisotropically through at least two layers of the material. Native chondral structures are distinguished by their multi-layered structure. By the material according to the invention combining several different layers, which moreover are traversed by anisotropic pores, the material not only corresponds to the natural (osteo) chondral matrix in structure, it can also reproduce the matrix with respect to the compositions of the layers.

In a further aspect the invention relates to the use of a multi-layered material as a meniscus support matrix, characterized in that pores extend anisotropically through at least two layers of the material. The multi-layered porous material can be produced in the form of a meniscus by the process according to the invention. The structure of a natural meniscus is distinguished by the different composition of the outer and the inner region of the meniscus and by the arrangement of the collagen fibrils running parallel to the peripheral edge. This structure is reproduced by the different layers and the orientation of the pores in the support matrix. Thus, curved or slanting structures are formed by central crystals being overgrown by adjacent crystals during the solidification. Such a structure can be obtained, for example, by using substances which have a relatively high viscosity and are temperature-controlled beforehand. The temperature control of the substances should be close to the temperature level of the warmer temperature-controllable body, for example 0.5° C. to 5° C. above the temperature level of the warmer temperature-controllable body. In this manner, after sublimation curved or slanted pores at an angle of up to 90° to the temperature gradient are obtained.

A further aspect the invention relates to the use of a multi-layered material as an intervertebral disc support matrix in which pores extend anisotropically through at least two layers of the material. Both materials with layers arranged above one another and those with layers arranged side by side or concentrically can be produced by the process according to the invention. The latter are suitable above all for an intervertebral disc support matrix. In accordance with the natural intervertebral disc, such a support matrix has an inner layer which corresponds to the nucleus pulposus, and layers arranged concentrically around this which correspond to the inner and the outer annulus fibrosus. By using substances having different compositions, the particular layers can be adapted to the physical properties of the different regions of an intervertebral disc. In order to reproduce the porosity of the natural intervertebral disc, the inner layer has isotropic pores, whereas the layers of the inner and outer annulus fibrosus have anisotropic pores. This promotes the stability of the matrix and its integration into natural tissue.

In a further aspect the invention relates to a process for the production of a multi-layered (osteo)chondral support matrix, comprising the steps of providing a temperature gradient by two temperature-controllable bodies arranged opposite one another; arranging and solidifying in the temperature gradient a first substance which contains at least one polymer, at least one glycosaminoglycan and at least one sublimable compound in order to form a middle chondral zone; arranging and solidifying in the temperature gradient a second substance which contains at least one polymer, at least one glycosaminoglycan and at least one sublimable compound in order to form a lower chondral zone directly adjacent to the middle chondral zone; optionally arranging and solidifying in the temperature gradient a third substance which contains at least one polymer, at least one alkaline earth metal phosphate and at least one sublimable compound in order to form a subchondral zone directly adjacent to the lower chondral zone; subliming the compound and consolidating the layers.

Both multi-layered chondral support matrices (without a subchondral zone) and osteochondral support matrices (with a subchondral zone) can be produced by the process. The support matrices are suitable in particular for treatment of chondral or osteochondral defects, since the chemical composition of the individual layers correspond to the natural layers of cartilage, that is to say the upper chondral zone, the lower chondral zone and the subchondral zone (FIG. 2). Analogously to the constituents of the natural chondral matrix, the substances for formation of the upper and lower chondral zone contain at least one polymer and at least one glycosaminoglycan and the substance for formation of the subchondral zone contains at least one polymer and at least one alkaline earth metal phosphate. The scaffold of the extracellular matrix of the native articular cartilage substantially consists of a subchondral zone containing calcium phosphate (transition zone to the bone), from which collagen fibres project (FIG. 2). In deeper-lying chondral areas (d) these are orientated normally to the bone surface, in the middle areas (m) this converts into a slanted fibre arrangement, which in turn when close to the surface (s) runs parallel to this. Together with the collagen fibre structure, the manifestation of the chondral cells (chondrocytes) and therefore also that of their cell associates (chondrones) also changes. While the chondrocytes in the deeper (d) and middle (m) chondral areas are round in shape and form columnar chondrones, in the upper chondral zone (s) they have a flat shape, and are combined in the form of horizontally running chondrones.

After the sublimation the monolithic matrix is consolidated, for example by being subjected to wet chemical crosslinking by means of activated carbodiimides, isocyanates, complexing ions, non-enzymatic glycation or glutaraldehyde. Preferably, the crosslinking is carried out by means of N-hydroxysuccinimide and 1-ethyl-3-(3-dimethylaminopropyl)carbodiimide with buffering by 2-morpholinoethanesulphonic acid. In this cell-compatible "zero-length" crosslinking covalent bonds are formed between the collagens, without further compounds being incorporated. Further preferred, the support matrix is pre-crosslinked dehydrothermally before the wet chemical crosslinking, for example under pressures of between $1*10^{-6}$ mbar and 100 mbar and at temperatures of between 50° C. and 200° C.

In a preferred embodiment the process further comprises the step of arranging a layer of functionalized polymer fibres on the support matrix. The layer of functionalized polymer fibres forms a friction-reducing surface which corresponds to the articular inside of native cartilage. It can be generated by functionalized polymer fibres (e.g. collagen type I, II, III, V, VI, IX, X, XI, XII, XIV, XVI, or linear, branched and star-shaped polymers based on polyethylene glycol), which form a final sliding layer (CS). The layer of functionalized polymer fibres can be applied to the material by means of electrostatic spinning, before or after consolidation thereof.

Due to the aligned solidification, the multi-layered chondral support matrix is traversed by anisotropic pores. As a result an efficient cell migration into the inside of the matrix is ensured, which contributes decisively towards complete integration of the support matrix into the defective cartilage and the functionality thereof. A further improvement in the population by cells can be obtained by a matrix compression. This is to be understood as meaning a deformation of the support structure which is caused by external mechanical pressure and exerts a suction effect on the cells on the basis of the capillary forces which arise, and draws these into the inside of the matrix.

In a preferred embodiment the at least one polymer which is present in the first, second and/or third substance, independently of each other, is a collagen selected from the group consisting of collagen type I, II, III, V, VI, IX, X, XI, XII, XIV, XVI, preferably collagen type I or type II. Collagens are the natural structural proteins of cartilage and form the predominant solids content of all the zones of natural cartilage. Collagens which are obtained from mammals and purified are suitable for the preparation of the substances of the precursors of the individual layers. Collagens which have been broken down by enzymatic cleavage and comminuted purified cartilage fragments and collagen fibrils are specifically suitable. Preferably, the substances comprise 0.5 to 60 wt. %, further preferred 0.8 to 10 wt. % of collagens.

In a preferred embodiment the at least one glycosaminoglycan which is present in the first and/or second substance, independently of each other, is selected from the group consisting of chondroitin sulphate, aggrecan, keratan sulphate, hyaluronic acid, proteoglycan 4, cartilage oligomeric matrix protein (COMP), fibromodulin, procollagen II, decorin, anchorin, hyaluronate, biglycan, thrombospondin, fibronectin and chondrocalcin. Preferably, the dry matter content of the substance layers has a content of glycosaminoglycans of from 1 to 35% a higher content of glycosaminoglycans leading to an increased resistance to compressions of the support matrix.

In a preferred embodiment the at least one alkaline earth metal phosphate contained in the third substance is a calcium phosphate or a magnesium phosphate, preferably selected from the group consisting of bruschite, monetite, hydroxylapatite, α-tricalcium phosphate, β-tricalcium phosphate, whitlockite, struvite, newberite and farringtonite. Higher contents of alkaline earth metal phosphates increase the resistance of the support matrix to compressions. The alkaline earth metal phosphates can be present in the form of alkaline earth metal phosphate crystallites, alkaline earth metal phosphate substrates or in the form of composite materials. Alkaline earth metal phosphates can be obtained, for example, by a cement reaction, by 3D rapid prototyping of alkaline earth metal phosphate powders or starting substances thereof, or by aligned solidification with subsequent sintering of substances comprising alkaline earth metal phosphate. Alkaline earth metal phosphate composite materials can be produced, inter alia, by bioplotting of a mixture of polymers and alkaline earth metal phosphate, or compounds which react to give alkaline earth metal phosphates.

In a preferred embodiment the first, second and/or third substance layer, independently of each other, contains antibiotics and/or growth factors, such as, for example, TGF, BMP, GDF, IGF, annexin and MMP. By the entire production process taking place exclusively at low temperatures, it is particularly suitable for integration of medicinal active compounds, which are usually heat-sensitive, into the individual layers of the support matrix. The active compounds can also be present in encapsulated form within the substances.

In a preferred embodiment the sublimable compound is acetic acid. Acetic acid is particularly preferred as the sublimable compound since as a weak acid it impairs protein structures less severely than strong acids, and the residues thereof can readily be removed by sublimation and have a comparatively good cell tolerability. The higher the concentration of collagen to be dissolved, the higher the molarities of acetic acid employed. In a particularly preferred embodiment the sublimable compound therefore contains 0.25-4 M acetic acid, preferably 0.5-3 M acetic acid, further preferred 0.5 M acetic acid.

In a preferred embodiment the first, second and/or third substance contains 0.5-60 wt. % of polymer, preferably 0.8-10 wt. % of polymer, further preferred 1-5 wt. % of polymer. Higher polymer contents lead to a more stabile structure of the support matrix and are therefore preferred in particular for use in joints which are subjected to load by the body weight, for example knee joints.

In a preferred embodiment the temperature gradient for the production of (osteo)chondral support matrices is between 5 and 10 K/mm, preferably 8 K/mm.

The support matrix is suitable in particular for treatment of chondral and osteochondral defects, both in the form of matrix-coupled autologous chondrocyte transplantation (MACT) and at the time of implantation of cell-free matrix. The support matrix according to the invention can moreover be employed for cell cultivation.

In a further aspect the invention relates to a process for the production of a multi-layered meniscus support matrix, comprising the steps of providing a temperature gradient by two temperature-controllable bodies arranged opposite one another; arranging and solidifying in the temperature gradient a first substance which contains collagen I, at least one glycosaminoglycan and at least one sublimable compound in order to form an outer meniscus region; arranging and solidifying in the temperature gradient a second substance which contains collagen I, collagen II, at least one glycosaminoglycan and at least one sublimable compound in order to form an inner meniscus region directly adjacent to the outer meniscus region; subliming the compound and consolidating the support matrix.

Figure 5:
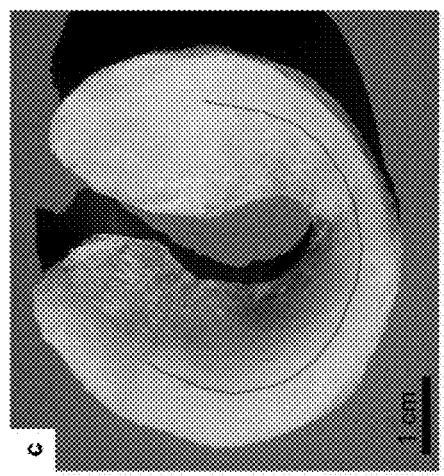
FIG. 5 shows a schematic representation of a support matrix for treatment of meniscus defects (a), the geometry of a temperature-controllable body (bottom) and an insulating body (top) for the production of such a support matrix (b) and an alginate model of a lateral meniscus (c). The line drawn in the part image c illustrates the course of the pore structure. The support matrix consists of an outer meniscus region (OM) and an inner meniscus region (IM), which differ in their chemical compositions.
Figure 5:
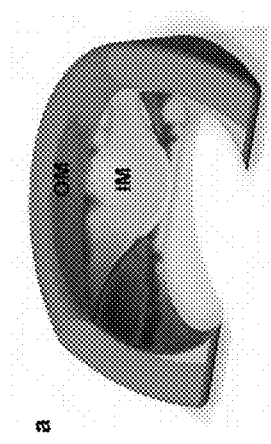
Figure 5:
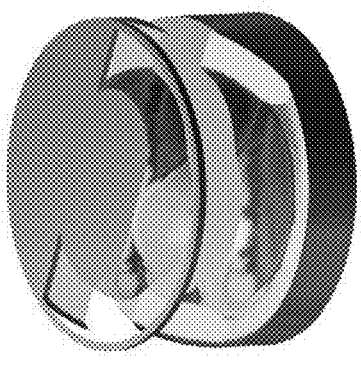

The support matrix obtained by the process corresponds to the natural meniscus both in its composition and in its microstructure. Temperature-controllable and insulating bodies or a container which correspond(s) to the negative form of a meniscus are used for solidification of the substances (FIG. 5 b). The meniscus-like outer manifestation of the support matrix is thereby obtained (FIG. 5 c). Due to the different layers of the support matrix, the outer and inner meniscus region is reproduced (FIG. 5 a). The orientation of the pores in the support matrix reproduces the arrangement of the collagen fibrils of the natural meniscus running parallel to the peripheral edge.

After the sublimation the monolithic matrix is consolidated, for example by being subjected to wet chemical crosslinking by means of activated carbodiimides, isocyanates, complexing ions, non-enzymatic glycation or glutaraldehyde. Preferably, the crosslinking is carried out by means of N-hydroxysuccinimide and 1-ethyl-3-(3-dimethylaminopropyl)carbodiimide with buffering by 2-morpholinoethanesulphonic acid. In this cell-compatible "zero-length" crosslinking covalent bonds are formed between the collagens, without further substances being incorporated. Further preferred, the support matrix is pre-crosslinked dehydrothermally before the wet chemical crosslinking, for example under pressures of between $1*10^{-6}$ mbar and 100 mbar and at temperatures of between 50° C. and 200° C.

In a preferred embodiment the process further comprises the step of arranging a layer of functionalized polymer fibres on the support matrix. These polymer fibres correspond to a friction-reducing outer layer of the natural meniscus, which forms a final sliding layer on the surface. The layer of functionalized polymer fibres can be applied to the material by means of electrostatic spinning, before or after consolidation thereof.

In a preferred embodiment the temperature gradient for the production of meniscus support matrices is between 3 and 8 K/mm, preferably 5 K/mm.

The support matrix is suitable for treatment of meniscus defects. The process according to the invention enables to produce a meniscus replacement according to the individual circumstances of the patient's joints. For this, the temperature-controllable and insulating bodies or a container which determines the form of the support matrix is produced according to three-dimensional reconstructions of the meniscus defect of the patient. This form is used in order to produce an accurately fitting support matrix.

In a further aspect the invention relates to a process for the production of a multi-layered intervertebral disc support matrix, comprising the steps of providing a temperature gradient by two temperature-controllable bodies arranged opposite one another; arranging a first layer which forms a core and is formed from a first substance which contains at least one polymer, at least one glycosaminoglycan and at least one sublimable compound; arranging and solidifying in the temperature gradient a second substance which contains at least one polymer, at least one glycosaminoglycan and at least one sublimable compound in order to form an inner layer directly adjacent to the core; arranging and solidifying in the temperature gradient a third substance which contains at least one polymer, at least one glycosaminoglycan and at least one sublimable compound in order to form an outer layer directly adjacent to the inner layer; subliming the compound and consolidating the layers.

Figure 7:
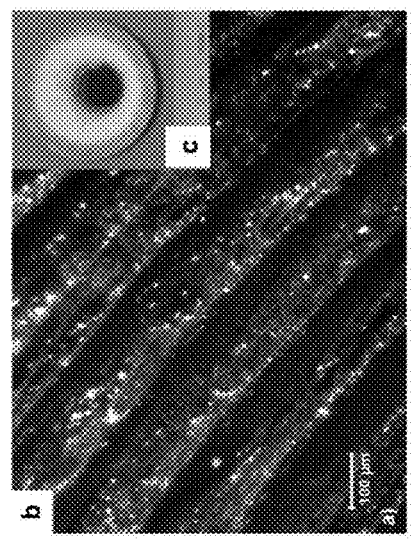
FIG. 7 a shows the schematic representation of a support matrix for treatment of intervertebral disc defects. Analogously to native tissue, the support matrix has constituents of the extracellular cartilage matrix, which are combined into a biomimetic, monolithic matrix. A non-aligned network which corresponds to the nucleus pulposus (NP) is to be found within a fibre arrangement of lamellar structure produced by aligned solidification, which corresponds to the annulus fibrosus. This is in turn divided into an outer annulus fibrosus (oAF) and an inner annulus fibrosus (iAF). The detailed view shows the main structure of the microstructure of the annulus fibrosus, which consists of individual lamellae joined to one another.
Figure 7:
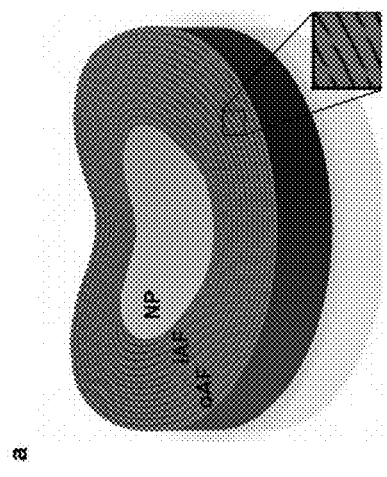

The natural intervertebral disc structure substantially consists of an inner core, the nucleus pulposus, which is enclosed by fibrous lamellae which form the annulus fibrosus (FIG. 7 a). The nucleus pulposus (NP) is structurally and mechanically isotropic and contains a proteoglycan-containing network of collagen type II. The annulus fibrosus consists of a large number of lamellae which consist of collagen type I in the outer part (outer annulus fibrosus, oAF) and collagen type II in the inner part (inner annulus fibrosus, iAF). Together with the inner intervertebral disc structure, the manifestation of the cells which occur in the intervertebral disc also changes. While the notochordal cells in the nucleus pulposus are round in shape, the cells in the inner annulus fibrosus are chondrocytic. The cells in the outer annulus fibrosus are described as fibrochondrocytes. Analogously to native tissue, the support matrix has constituents of the extracellular chondral matrix, which are combined into a biomimetic, monolithic support matrix. A non-aligned network is to be found in the core of the matrix and corresponds to the nucleus pulposus. This is surrounded by two layers of different composition, which have a lamellar structure and correspond to the inner and outer annulus fibrosus.

After the sublimation the monolithic matrix is consolidated, for example by being subjected to wet chemical crosslinking by means of activated carbodiimides, isocyanates, complexing ions, non-enzymatic glycation or glutaraldehyde. Preferably, the crosslinking is carried out by means of N-hydroxysuccinimide and 1-ethyl-3-(3-dimethylaminopropyl)carbodiimide with buffering by 2-morpholinoethanesulphonic acid. In this cell-compatible "zero-length" crosslinking covalent bonds are formed between the collagens, without further substances being incorporated. Further preferred, the support matrix is pre-crosslinked dehydrothermally before the wet chemical crosslinking, for example under pressures of between $1*10^{-6}$ mbar and 100 mbar and at temperatures of between 50° C. and 200° C.

In a preferred embodiment the process further comprises the step of arranging a layer of functionalized polymer fibres on the support matrix. These polymer fibres correspond to the outer membrane which surrounds the natural intervertebral disc. The layer of functionalized polymer fibres can be applied to the material by means of electrostatic spinning, before or after consolidation thereof.

In a preferred embodiment the at least one polymer which is present in the first, second and/or third substance, independently of each other, is a collagen selected from the group consisting of collagen type I, II, III, V, VI, IX, X, XI, XII, XIV, XVI, cellulose, chitosan, polylactic acid (D and/or L) or polyglycollic acid, polycaprolactone and polyethylene glycol, preferably collagen type I or type II. Collagens are the natural structural proteins of cartilage and form the predominant solids content of all the zones of natural cartilage. Collagens which are obtained from mammals and purified are suitable for the preparation of the substances of the precursors of the individual layers. Collagens which have been broken down by enzymatic cleavage and comminuted purified cartilage fragments and collagen fibrils are specifically suitable. In a further preferred embodiment the first substance contains collagen type II, the second substance collagen type II and the third substance collagen type I.

In a preferred embodiment the at least one glycosaminoglycan which is contained in the first, second and/or third substance, independently of each other, is selected from the group consisting of chondroitin sulphate, aggrecan, keratan sulphate, hyaluronic acid, proteoglycan 4, cartilage oligomeric matrix protein (COMP), fibromodulin, procollagen II, decorin, anchorin, hyaluronate, biglycan, thrombospondin, fibronectin and chondrocalcin. Preferably, the dry matter content of the substances for the production of intervertebral disc support matrices has a content of glycosaminoglycans of from 10 to 55%, a higher content of glycosaminoglycans leading to an increased resistance of the support matrix to compressions.

In a preferred embodiment the first, second and/or third substance layer, independently of each other, contains antibiotics and/or growth factors, for example, TGF, BMP, GDF, IGF, annexin and MMP. By the entire production process taking place exclusively at low temperatures, it is particularly suitable for integration of medicinal active compounds, which are usually heat-sensitive, in the individual layers of the support matrix. The active compounds can also be present in encapsulated form within the substances.

In a preferred embodiment the sublimable compound is acetic acid. Acetic acid is particularly preferred as the sublimable compound since as a weak acid it impairs protein structures less severely than strong acids, and the residues thereof can readily be removed by sublimation and have a comparatively good cell tolerability. The higher the concentration of collagens to be dissolved, the higher the molarities of acetic acid employed. In a particularly preferred embodiment the sublimable compound therefore contains 0.25-4 M acetic acid, preferably 0.5-3 M acetic acid, further preferred 0.5 M acetic acid.

In a preferred embodiment the first, second and/or third substance contains 0.5-60 wt. % of polymer, preferably 0.8-20 wt. % of polymer, further preferred 1-15 wt. % of polymer. Higher polymer contents lead to a more stable structure of the support matrix.

In a preferred embodiment the dry matter of the first, second and/or third substance, independently of each other, contains 5%-65% of glycosaminoglycans, such as, for example, chondroitin sulphate. In a further preferred embodiment the dry matter of the first substance (NP precursor) contains 10%-65% of glycosaminoglycans, the dry matter of the second substance (iAF precursor) contains 10%-55% of glycosaminoglycans and the dry matter of the third substance (oAF precursor) contains 5%-30% of glycosaminoglycans.

In a preferred embodiment for the production of intervertebral disc support matrices the temperature gradient is between 0.25 K/mm and 10 K/mm.

In a preferred embodiment the interpolated solidification rate is from $0.1 \times 10^{-2}$ mm/s to $10 \times 10^{-2}$ mm/s.

In a preferred embodiment the first layer is formed by wet chemical crosslinking. This is carried out, for example, by addition of a carbodiimide solution. The carbodiimide solution is present in the form of an ethanol/water mixture which contains 5-40 mM N-hydroxysuccinimide, 50-250 mM 1-ethyl-3-(3-dimethylaminopropyl)carbodiimide and 100-350 mM 2-morpholinoethanesulphonic acid. The pre-consolidated NP precursor is then placed within a container which contains a further shaping, insulating body, and the free space between the pre-consolidated NP precursor and the insulating body is filled with the second substance (iAF precursor).

In an alternative embodiment the first layer is formed by solidifying the first substance in a non-aligned form, for example at a uniform temperature or a very small temperature gradient of <0.5 K/mm. For this, the substance for production of the NP zone (NP precursor) is solidified, for example, in a non-aligned form within a shaping insulating body, which in turn can be within a container. After conclusion of the non-aligned solidification, the insulating body can be removed from the container and replaced by a further shaping insulating body.

The space thereby formed is filled with the iAF precursor and the precursors are solidified. The pre-consolidated NP precursor is thereby solidified in a non-aligned form, while the iAF precursor is solidified in an aligned form. After conclusion of the aligned solidification, the insulating body can be removed from the container. After the solidification of the second substance (iAF precursor), the insulating body is removed and the third substance (oAF precursor) is arranged in the free space and solidified in an aligned form.

In a preferred embodiment the solidification of the precursors is carried out within a microstructured container. The formation of crystallization nuclei of the sublimable additives preferentially arises at points on the container base which are determined by the microstructuring. Due to a corresponding microstructuring, the spatial orientation of the solidification forms of the sublimable additives is controlled. This leads, for example, to lamellar structures of the precursors solidified in an aligned form (iAF and oAF), which concentrically enclose the precursor solidified in a non-aligned form (NP).

The support matrix is suitable for treatment of intervertebral disc defects, for example in the form of matrix-coupled cell transplantation. The support matrix according to the invention can moreover be employed for cell cultivation.

EXAMPLES

1. Construction of the Solidification Apparatus

The solidification apparatus is constructed as shown in FIG. 1. Peltier elements coupled to heat exchangers generate a temperature gradient which is controlled by regulation of the flow of current in the Peltier elements. Successive precursors (e.g. subchondral (SC) suspension, deep chondral zone (CD) suspension and middle chondral zone (CM) suspension) are introduced into the sample chamber and thus placed within the temperature gradient. Due to the temperature gradient a unidirectional growth of ice crystals occurs within the precursors. The apparatus can further contain temperature-controllable bodies, as well as a container containing the precursors.

The sample chamber (FIG. 1 b) is in the centre of the insulation unit I1 and is in thermal contact with the temperature-controllable bodies W1 and W2, which are located both above and below the sample chamber. The temperature-controllable bodies W1 and W2 are within the insulation unit I2 and are coupled to the Peltier elements P1 and P2, which are fixed by the insulation units I3 and I4. This inner assembly is in the centre of the heat exchanger ring A2, which together with the heat exchanger units A1 and A3 forms an outer assembly.

2. Osteochondral Support Matrix for Treatment of Articular Chondral Defects

2.1. Preparation of the Precursors

The precursors of the individual layers which reproduce the middle chondral zone, the deep chondral zone and the subchondral zone had the following compositions:

middle chondral zone (CM):
  1.0 wt. % of collagen type II
  0.16 wt. % of chondroitin sulphate and
  0.5 M acetic acid as the sublimable compound;
deep chondral zone (CD):
  1.0 wt. % of collagen type II
  0.2 wt. % of chondroitin sulphate and
  0.5 M acetic acid as the sublimable compound;
subchondral zone (SC)
  0.8 wt. % of collagen type I
  0.8 wt. % of absorbable calcium phosphate phase bruschite and
  0.5 M acetic acid as the sublimable compound.

Lyophilized collagen type II or collagen type I was used for the preparation of the individual precursors. The constituents of the precursors were stirred in acetic acid at room temperature for 30 min and then left to swell for 24 h at 5° C. Before use, the precursors were temperature-controlled at 15° C. beforehand.

2.2 Freeze-Structuring of the Precursors

The freeze-structuring was carried out with a solidification apparatus as described in Example 1. A polystyrene cell culture dish was employed as a container for accommodating the precursors in the inner constructional unit of the solidification apparatus. By electrical regulation of the Peltier elements, an external temperature gradient of 8 K/mm with $T_{Peltier1}$ −40° C. (lower Peltier element) and $T_{Peltier2}$ 24° C. (upper Peltier element) was established. As soon as the inner constructional unit and the container were close to thermal equilibrium, 2 ml of the precursor for the subchondral zone were injected into the container and solidified for 20 min. 2 ml of the precursor of the deep chondral zone were then injected into the container, so that the deep chondral zone was formed directly on the subchondral zone. After a further 20 min 2 ml of the precursor of the upper chondral zone were injected into the container, i.e. directly on to the lower chondral zone. The precursors were solidified for a further 20 min.

The container with the solidified precursors was then removed from the solidification apparatus and if appropriate intermediately stored at −20° C.

2.3 Lyophilization of the Precursors Solidified in an Aligned Manner

The container with the solidified precursors was introduced into the working volume of a running lyophilizer. The solidified precursors were lyophilized under a pressure of 0.08 mbar and at a temperature of −60° C. for 24 h. The solidified sublimable constituents of the precursors were thereby sublimed out of these and removed.

2.4 Consolidation of the Material

The solidified precursors were pre-crosslinked by a dehydrothermal process under a pressure of 0.08 mbar and at a temperature of 105° C. for 210 min. The material was then consolidated further by wet chemical crosslinking. For this, the solidified and pre-crosslinked precursors were placed in a pressure container and, after the working pressure of 100 mbar was reached, 100 µl/mg of material of a carbodiimide solution were added. A 2:3 ethanol/water mixture which contained 21 mM N-hydroxysuccinimide, 52 mM 1-ethyl-3-(3-dimethylaminopropyl)carbodiimide and 200 mM 2-morpholinoethanesulphonic acid was used as the carbodiimide solution. 45 seconds after infiltration of the material pores the pressure container was ventilated. After a reaction time of 24 h the support matrix was washed three times in distilled water.

2.5 Application of Functionalized Polymer Fibres

Functionalized polymer fibres were applied as a friction-reducing surface (CS) to the middle chondral zone of the support matrix. These were applied to the material by means of electrostatic spinning, after consolidation thereof. The experimental procedure was carried out as described in Grafahrend et al. (2010).

2.6 Properties of the Support Matrix

Figure 3:
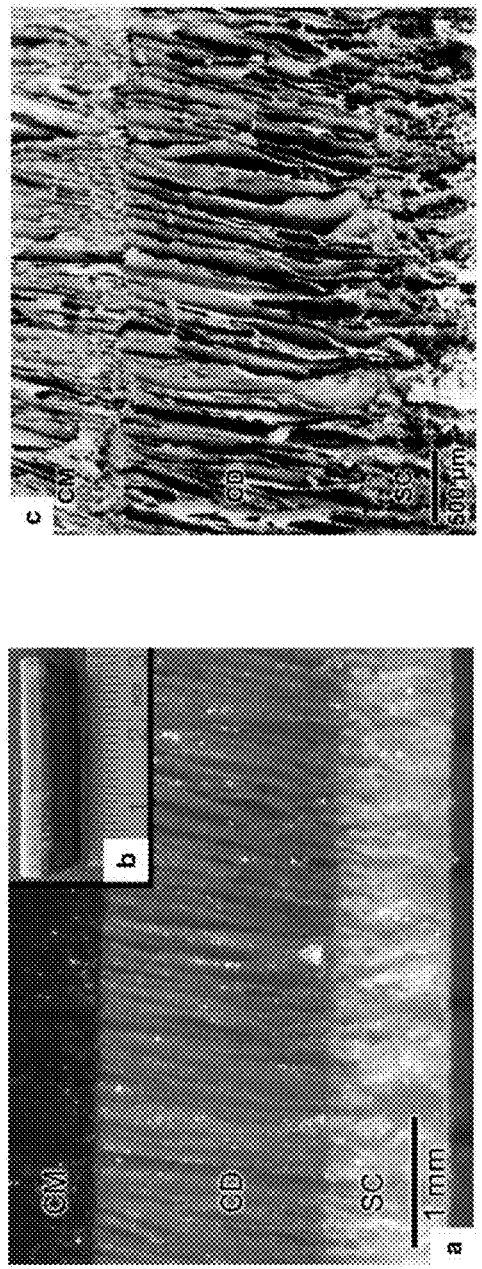
FIG. 3 shows light microscopy (a), a photographic (b) and an electron microscopy image (c) of a monolithic, osteochondral alginate-based support structure. Anisotropic pores having a cross-section in the region of 80 μm in size run continuously through the individual zones of the chondral part (CM—upper zone shown as dark and CD—middle zone shown in grey) and through the subchondral part (SC—lower zone shown in white). The subchondral part is mineralized by the absorbable calcium phosphate phase bruschite. Individual zones were produced with coloured precursors.
Figure 4:
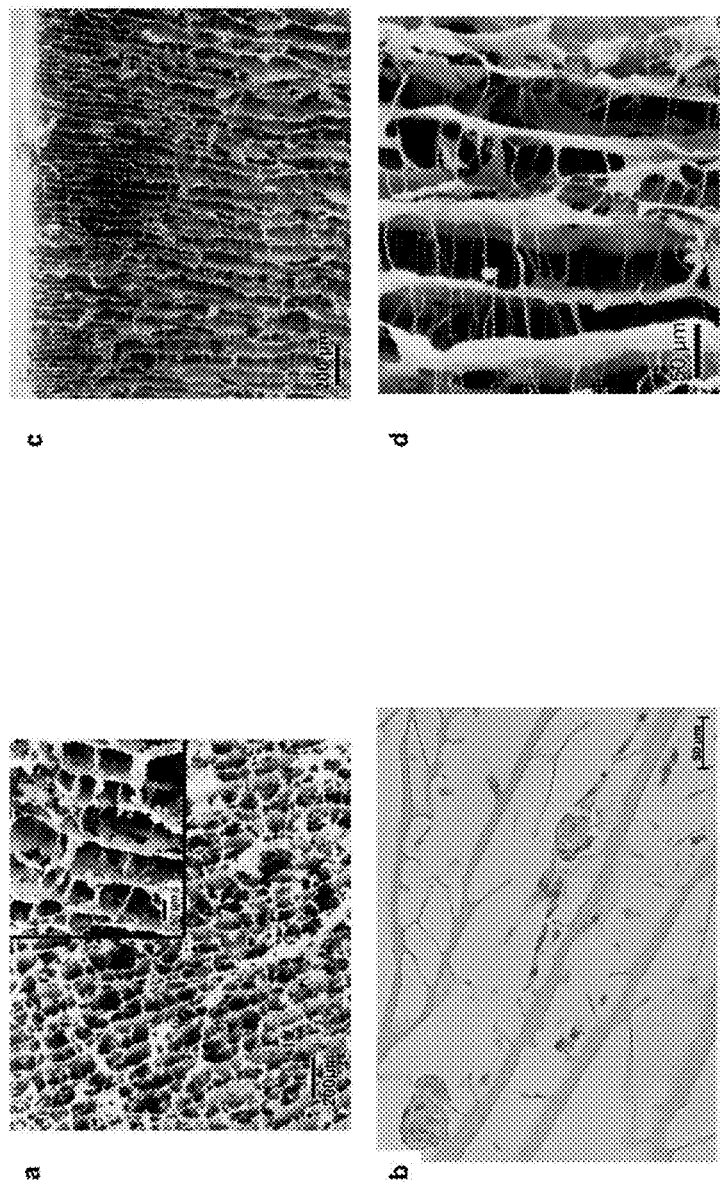
FIG. 4 a shows an electron microscopy image of the surface of a chondral support matrix produced according to Example 2.
Figure 8:
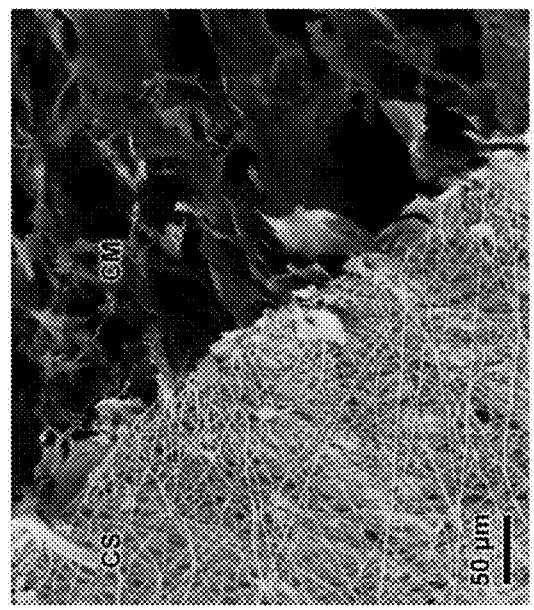
FIG. 8 shows a scanning electron microscopy sectional image of functionalized polymer fibres which form the final sliding layer (CS) of an underlying osteochondral support matrix and are joined to the middle chondral zone (CM). The polymer fibres run orthogonally to the pore structure of the remaining support matrix and in this way reproduce the fibre arrangement of native osteochondral tissue.

The finished four-layered support matrix reproduces native cartilage, and comprises a subchondral zone, a deep chondral zone, a middle chondral zone and a friction-reducing surface (FIGS. 2, 3 and 8). Light microscopy and electron microscopy images of the support matrix show elongated anisotropic pores thereof both in the alginate model (Example 6, FIG. 3) and in the collagen support matrix (FIG. 4). These structures are formed by the aligned crystals of acetic acid which were formed by solidification of the precursors and subsequent sublimation thereof. The fibre structure of the friction-reducing surface runs perpendicular to this pore structure. (FIG. 8)

3. Osteochondral Support Matrix for Treatment of Articular Chondral Defects 3.1 Preparation of the Precursors The precursors of the individual layers which reproduce the middle chondral zone, the deep chondral zone and the subchondral zone had the following compositions:
middle chondral zone (CM):
  2.5 wt. % of collagen type II
  0.5 wt. % of chondroitin sulphate and
  0.5 M acetic acid as the sublimable compound;
deep chondral zone (CD):
  2.5 wt. % of collagen type II
  0.8 wt. % of chondroitin sulphate and
  0.5 M acetic acid as the sublimable compound;
subchondral zone (SC)
  1.0 wt. % of collagen type I
  0.5 wt. % of absorbable calcium phosphate phase bruschite and
  0.5 M acetic acid as the sublimable compound.

The individual precursors were prepared as in Example 2.

3.2 Freeze-Structuring of the Precursors

The freeze-structuring was carried out as described in Example 2 at an external temperature gradient of 6.25 K/mm with $T_{Peltier1}$ −32° C. (lower Peltier element) and $T_{Peltier2}$ 7.5° C. (upper Peltier element) and an interpolated solidification rate following from this of $0.27 \times 10^{-2}$ mm/s.

3.3 Lyophilization of the Precursors Solidified in an Aligned Manner

The lyophilisation was carried out as described in Example 2 under a pressure of 0.08 mbar and at a temperature of −60° C. for 17 h.

3.4 Consolidation of the Material

The consolidation of the material was carried out as described in Example 2.

4. Support Matrix for Treatment of Meniscus Defects 4.1 Preparation of the Precursors The precursors of the individual layers which reproduce the outer (OM) and the inner meniscus region (IM) (FIG. 5 *a*) had the following compositions:
outer meniscus region (OM):
  1.5 wt. % of collagen type I
  0.012 wt. % of chondroitin sulphate and
  0.5 M acetic acid as the sublimable compound;
inner meniscus region (IM):
  1.8 wt. % of collagen type II
  1.2 wt. % of collagen type I
  0.06 wt. % of chondroitin sulphate and
  0.5 M acetic acid as the sublimable compound.

The individual precursors were prepared as in Example 2.

4.2 Freeze-Structuring of the Precursors

The freeze-structuring was carried out with a solidification apparatus as described in Example 1. A container which represented the negative form of a meniscus (FIG. 5 *b*) and contained an insulating body functioning as a place-holder for the inner meniscus region was inserted into the inner constructional unit of the solidification apparatus. The precursor of the outer meniscus region was first introduced into this container and solidified. The insulating body was then removed and the precursor of the inner meniscus region was introduced and solidified. Due to the form of the container, the support structure formed acquired the form of a meniscus (FIG. 5 *c*).

By electrical regulation of the Peltier elements, an external temperature gradient of 4.5 K/mm with $T_{Peltier1}$=−20° C. (lower Peltier element) and $T_{Peltier2}$=16° C. (upper Peltier element) was established. An insulating body which served as a place-holder and had the form of the inner meniscus region was placed in the container. As soon as the inner constructional unit and the container with the insulating body were close to thermal equilibrium, 4 ml of the precursor for the outer meniscus region were injected into the container and solidified for 25 min. The inner edge of the outer meniscus region was thereby formed. After solidification of the precursor of the outer meniscus region, the place-holder was removed from the container and 2 ml of the precursor for the inner meniscus region were injected into the container so that the inner meniscus region was formed directly on the outer meniscus region. The precursors were solidified for a further 15 min.

The container with the solidified precursors was then removed from the solidification apparatus and if appropriate intermediately stored at −20° C. until the further processing.

4.3 Lyophilization of the Precursors Solidified in an Aligned Manner

The lyophilisation was carried out as described in Example 2 under a pressure of 0.08 mbar and at a temperature of −60° C. for 24 h.

4.4 Consolidation of the Material

The consolidation of the material was carried out as described in Example 2.

4.5 Properties of the Support Matrix

Figure 6:
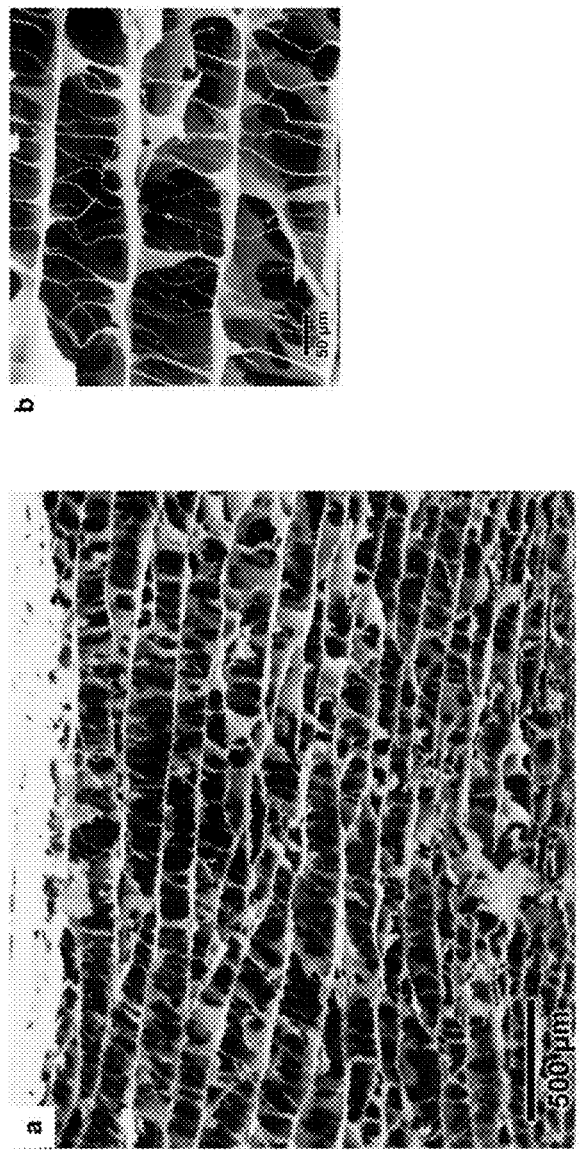
FIG. 6 shows scanning electron microscopy images of a vertical section through a collagen support matrix for treatment of meniscus defects (Example 4).

The finished two-layered support matrix corresponds to the outer form (FIG. 5 c) and the inner structure of a native meniscus (FIG. 6 a, b). The support matrix is traversed by lamellar pores (FIG. 6 a, b). On solidification of the precursors of the meniscus regions overgrowing of the central crystals by adjacent crystals occurs, as a result of which lamellar pores corresponding to the native tissue structure run predominantly horizontally through the meniscus support matrix.

5. Support Matrix for Treatment of Intervertebral Disc Defects 5.1 Preparation of the Precursors The precursors of the individual layers which reproduce the nucleus pulposus (NP), the inner annulus fibrosus (iAF) and the outer annulus fibrosus (oAF) had the following compositions:

nucleus pulposus (NP):
 4 wt. % of collagen type II
 2 wt. % of chondroitin sulphate and
 0.5 M acetic acid as the sublimable compound;
inner annulus fibrosus (iAF):
 2 wt. % of collagen type II
 0.8 wt. % of chondroitin sulphate and
 0.5 M acetic acid as the sublimable compound;
outer annulus fibrosus (oAF):
 1 wt. % of collagen type I
 0.15 wt. % of chondroitin sulphate and
 0.5 M acetic acid as the sublimable compound.

The individual precursors were prepared as in Example 2.

5.2 Freeze-Structuring of the Precursors

The freeze-structuring is carried out with a solidification apparatus as described in Example 1. A container which corresponds in form to an intervertebral disc is arranged in the inner constructional unit of the solidification apparatus. On the base of this container is a microstructure consisting of linear depressions. These spread out in the radial direction, starting from the region of the nucleus pulposus (NP). The microstructure serves as a crystallization point for the solidification of the precursors of the inner annulus fibrosus (iAF) and the outer annulus fibrosus (oAF).

The microstructured container was laid in the inner constructional unit of the solidification apparatus, insulating bodies functioning as place-holders for the iAF and oAF. The place-holders occupied approx. 36% of the volume available for production of the support matrix. By electrical regulation of the Peltier elements, an external temperature gradient of 0.25 K/mm was first established ($T_{Peltier1}$=−22° C.; $T_{Peltier2}$=−20° C.). As soon as the inner constructional unit together with the shaping bodies contained therein was close to thermal equilibrium, 0.7 ml of the precursor of the NP was filled into the centre of the container within the sample chamber and solidified for 15 min. By electrical regulation of the Peltier elements, an external temperature gradient of 8.5 K/mm was then established ($T_{Peltier1}$=−40° C.; $T_{Peltier2}$=28° C.). As soon as the inner constructional unit together with the shaping bodies contained therein was close to thermal equilibrium, the place-holder for the iAF precursor was removed and 1.2 ml of the precursor of the iAF were filled in between the layer corresponding to the NP and the insulating place-holder for the oAF precursor. The place-holder for the oAF precursor was located on the outer edge of the container and filled approx. 18% of the volume of the container. After a further 10 min of freeze-structuring the place-holder was removed and in its place 1.5 ml of the precursor of the oAF were fed in. After a further 10 min of freeze-structuring the container with the precursors solidified in a common aligned manner was removed and if appropriate intermediately stored at −20° C. until the further processing.

5.3 Lyophilization of the Precursors Solidified in an Aligned Manner

The lyophilisation was carried out as described in Example 2 under a pressure of 0.08 mbar and at a temperature of −60° C. for 17 h.

5.4 Consolidation of the Material

The consolidation of the material was carried out as described in Example 2.

5.5 Properties of the Support Matrix

Because of the only very small temperature gradient during the solidification of the support matrix region corresponding to the NP, non-aligned solidification occurs. As a result, this region has an isotropic pore structure. The regions of the iAF and the oAF which are adjacent to this, on the other hand, have a lamellar anisotropic pore structure due to the aligned solidification in the temperature gradient. Due to the microstructuring on the base of the container, the anisotropic pores show a pattern arranged concentrically around the region of the NP (FIG. 7 b).

6. Alginate Model for a Support Matrix for Treatment of Meniscus Defects 6.1 Preparation of the Precursors The precursors of the individual layers comprised, for model purposes, 5.5% alginate, dissolved in distilled water.

6.2 Freeze-Structuring of the Precursors

The freeze-structuring was carried out with a solidification apparatus as described in Example 1. A container which represented the negative form of a meniscus (FIG. 5 b) was inserted into the inner constructional unit of the solidification apparatus. The precursor of the outer meniscus region was first introduced into this container and solidified, and the precursor of the inner meniscus region was then introduced and solidified. Due to the form of the container, the support structure formed acquired the form of a meniscus (FIG. 5 c).

By electrical regulation of the Peltier elements, an external temperature gradient of 1.8 K/mm with $T_{Peltier1}$=−20° C. (lower Peltier element) and $T_{Peltier2}$=5° C. (upper Peltier element) was established. As soon as the inner constructional unit and the container with an insulating body which served as a place-holder and had the form of the inner meniscus region were close to thermal equilibrium, 8 ml of the precursor for the outer meniscus region were injected into the container and solidified for 30 min. The inner edge of the outer meniscus region was thereby formed. After solidification of the precursor of the outer meniscus region, the place-holder was removed from the container and 4 ml of the precursor for the inner meniscus region were injected into the container so that the inner meniscus region was formed directly on the outer meniscus region. The precursors were solidified for a further 15 min.

The container with the solidified precursors was then removed from the solidification apparatus and if appropriate intermediately stored at −20° C. until the further processing.

6.3 Lyophilization of the Precursors Solidified in an Aligned Manner

The lyophilisation was carried out as described in Example 2 under a pressure of 0.08 mbar and at a temperature of −60° C. for 24 h.

6.4 Consolidation of the Material

The consolidation of the material was carried out by wet chemical crosslinking. For this, the freeze-dried structure was placed in a pressure container and, after the working pressure of 100 mbar was reached, 50 µl/mg of material of a 1 M $CaCl_2$ solution were added. 45 seconds after infiltration of the material pores the pressure container was ventilated. After a reaction time of 24 h the support matrix was washed three times in distilled water.

7. Alginate Model for a Support Matrix for Treatment of Intervertebral Disc Defects

7.1 Preparation of the Precursors

The precursors of the individual layers consisted of, for model purposes, 5.5% alginate, dissolved in distilled water, and had different added dyes for visual differentiation of the individual layers. Before use, the precursors were temperature-controlled at 15° C. beforehand.

7.2 Freeze-Structuring of the Precursors

The freeze-structuring was carried out as described in Example 5.

7.3 Lyophilization of the Precursors Solidified in an Aligned Manner

The lyophilisation was carried out as described in Example 2 under a pressure of 0.08 mbar and at a temperature of −60° C. for 24 h.

7.4 Consolidation of the Material

The consolidation of the material was carried out as described in Example 6.

REFERENCES

A. Tampieri, M. Sandri, E. Landi, D. Pressato, S. Francioli, R. Quarto, et al., Biomaterials Design of graded biomimetic osteochondral composite scaffolds, Biomaterials. 29 (2008) 3539-3546.

T. J. Klein, S. C. Rizzi, J. C. Reichert, N. Georgi, J. Malda, W. Schuurman, et al., Strategies for Zonal Cartilage Repair using Hydrogels, Macromolecular Bioscience. 9 (2009) 1049-1058.

D. Grafahrend, K.-H. Heffels, M. V. Beer, P. Gasteier, M. Möller, G. Boehm, et al., Degradable polyester scaffolds with controlled surface chemistry combining minimal protein adsorption with specific bioactivation, Nature Materials. 10 (2010) 67-73.

DE 197 51 031 A1

EP 1 858 562 B1

The invention claimed is:

1. A process for the production of a multi-layered material having anisotropic pores, the process comprising the steps of:
   (a) providing a temperature gradient between two temperature-controllable bodies arranged opposite one another;
   (b) arranging in the temperature gradient a first substance containing at least one sublimable compound and solidifying the first substance to form a first layer;
   (c) arranging in the temperature gradient a second substance containing at least one sublimable compound adjacent to the first substance and solidifying the second substance to form a second layer adjacent to the first layer;
   (d) subliming the sublimable compounds of the adjacent first and second layers to form a monolithic support matrix of the first and second layers having pores generated by the subliming, the pores extending continuously and anisotropically throughout the first and second layers of the monolithic support matrix, and the pores penetrating the first and second layers of the support matrix; and
   (e) consolidating the support matrix,
   wherein the arranging of the second substance is conducted over the first substance, side-by-side with the first substance, or concentrically around the first substance without the solidifying of the first and second substances being interrupted.

2. The process of claim 1, wherein the temperature gradient is between 0.5 K/mm and 200 K/mm.

3. The process of claim 2, wherein the temperature gradient is between 2.5 K/mm and 25 K/mm.

4. The process of claim 2, wherein the temperature gradient is between 5 K/mm and 15 K/mm.

5. The process of claim 1, wherein the first and/or the second substance, independently of each other, contains at least one polymer or monomers thereof.

6. The process of claim 5, wherein the polymer is selected from the group consisting of peptides, proteins, polysaccharides, and mixtures thereof.

7. The process of claim 6, wherein the polymer is a protein, and the protein is a structural protein.

8. The process of claim 1, wherein the sublimable compound of the first and/or the second substance, independently of each other, is selected from the group consisting of aqueous solvents, polar solvents, non-polar solvents, organic acids, organic bases, mineral acids, and mineral bases.

9. The process of claim 1, wherein the sublimable compounds of the first substance and the second substance are the same sublimable compound.

10. The process of claim 1, wherein at least one of the temperature-controllable bodies has a microstructuring.

11. The process of claim 1, further comprising the step of: arranging a layer of functionalized polymer fibres on the support matrix as an outermost layer.

12. The process of claim 1, wherein the consolidating is carried out by wet chemical crosslinking, dehydrothermal processes, enzymatic crosslinking, non-enzymatic glycation, UV irradiation, gamma irradiation, sintering, infiltration, or a combination thereof.

13. The process of claim 1, wherein as a result of the solidifying of the second substance adjacent to the first substance, crystals of the sublimable compounds grow uniformly successively throughout the first and second layers, and wherein the crystals are removed as a result of the subliming so as to leave the continuous and anisotropic pore structure in the support matrix.

14. The process of claim 1, wherein the support matrix is a chondral support matrix, an osteochondral support matrix, a meniscus support matrix, or an intervertebral disc support matrix.

15. The process of claim 1, wherein the first and second layers of the support matrix differ in composition, functionality, and physical properties.

16. The process of claim 1,
   wherein step (c) further comprises arranging in the temperature gradient a third substance containing at least one sublimable compound adjacent to the second substance and solidifying the third substance to form a third layer adjacent to the second layer, wherein step (d) further comprises subliming the sublimable compound of the third layer to form the monolithic support matrix additionally of the third layer, the pores extending anisotropically throughout the first, second, and third layers of the monolithic support matrix, and the pores penetrating the first, second, and third layers of the support matrix, and wherein the arranging of the third substance is conducted without the solidifying of the first, second, and third substances being interrupted.

17. The process of claim 16, wherein the first, second, and third layers of the support matrix differ in composition, functionality, and physical properties.

18. The process of claim 16, wherein the arranging of the third substance is conducted over the second substance, side-by-side with the second substance, or concentrically around the second substance.

19. The process of claim 16, wherein the pores extend throughout the first, second, and third layers of the support matrix.

\* \* \* \* \*